(12) United States Patent
Darkin et al.

(10) Patent No.: US 8,640,698 B2
(45) Date of Patent: Feb. 4, 2014

(54) METHOD AND APPARATUS FOR MONITORING THE CONDITION OF A PATIENT WITH DIABETES

(75) Inventors: Donald Darkin, Kenthurst (AU); Klaus Henry Schindhelm, Glenhaven (AU); Carmel Therese Harrington, Coogee (AU)

(73) Assignee: RedMed Limited, Bella Vista (AU)

( * ) Notice: Subject to any disclaimer, the term of this patent is extended or adjusted under 35 U.S.C. 154(b) by 1419 days.

(21) Appl. No.: 11/997,976

(22) PCT Filed: Feb. 16, 2007

(86) PCT No.: PCT/AU2007/000172
§ 371 (c)(1),
(2), (4) Date: Feb. 5, 2008

(87) PCT Pub. No.: WO2007/093010
PCT Pub. Date: Aug. 23, 2007

(65) Prior Publication Data
US 2009/0007918 A1    Jan. 8, 2009

(30) Foreign Application Priority Data
Feb. 17, 2006    (AU) .................................. 2006900780

(51) Int. Cl.
*A61M 15/08* (2006.01)
*A61M 16/06* (2006.01)
*A61M 16/00* (2006.01)

(52) U.S. Cl.
USPC ............ 128/204.23; 128/207.18; 128/207.13; 128/204.21; 128/204.18; 128/200.26

(58) Field of Classification Search
USPC .......... 128/857, 863, 200.24, 204.18, 204.21, 128/204.23, 205.23, 205.25, 206.21; 600/365, 345, 347, 309, 484, 529; 514/866
See application file for complete search history.

(56) References Cited

U.S. PATENT DOCUMENTS

| 4,365,637 A | 12/1982 | Johnson |
| 4,875,477 A * | 10/1989 | Waschke et al. ......... 128/206.21 |
| 4,944,310 A | 7/1990 | Sullivan |

(Continued)

FOREIGN PATENT DOCUMENTS

| WO | WO 00/66209 | 11/2000 |
| WO | WO 2006/037184 | 4/2006 |

OTHER PUBLICATIONS

International Search Report for PCT/AU2007/000172 mailed Mar. 19, 2007.

(Continued)

*Primary Examiner* — Annette Dixon
(74) *Attorney, Agent, or Firm* — Nixon & Vanderhye PC

(57) ABSTRACT

According to certain example embodiments of this invention, there is provided an apparatus for treatment of a patient with both sleep-disordered breathing and diabetes. A PAP device may be configured to provide a supply of pressurized breathable gas. At least one glycemia sensor also may be provided. A controller may be operable to receive a signal from the at least one glycemia detector and may be further operable to analyze the signal for an indication of a glycemia abnormality (e.g., hypoglycemia, hyperglycemia, diabetic coma, etc.). Optionally, when the signal indicates that the patient is experiencing a diabetic event, an alert may be generated and/or a drug delivery unit may administer an appropriate treatment to the patient.

26 Claims, 3 Drawing Sheets

(56) References Cited

U.S. PATENT DOCUMENTS

| | | | |
|---|---|---|---|
| H0001039 H * | 4/1992 | Tripp et al. | 128/206.28 |
| 5,704,345 A | 1/1998 | Berthon-Jones | |
| 6,062,216 A * | 5/2000 | Corn | 128/204.23 |
| 6,199,550 B1 * | 3/2001 | Wiesmann et al. | 128/204.23 |
| 6,349,724 B1 * | 2/2002 | Burton et al. | 128/204.18 |
| 6,572,542 B1 * | 6/2003 | Houben et al. | 600/300 |
| 6,596,261 B1 * | 7/2003 | Adjei et al. | 424/45 |
| 6,770,037 B2 * | 8/2004 | Sullivan et al. | 600/529 |
| 6,882,940 B2 | 4/2005 | Potts et al. | |
| 6,934,571 B2 * | 8/2005 | Wiesmann et al. | 600/326 |
| 7,024,235 B2 * | 4/2006 | Melker et al. | 600/340 |
| 7,052,472 B1 * | 5/2006 | Miller et al. | 600/549 |
| 7,054,680 B1 * | 5/2006 | Genger et al. | 600/544 |
| 7,127,278 B2 * | 10/2006 | Melker et al. | 600/340 |
| 7,204,250 B1 * | 4/2007 | Burton | 128/205.23 |
| 7,575,005 B2 * | 8/2009 | Mumford et al. | 128/205.23 |
| 7,848,794 B2 * | 12/2010 | Genger et al. | 600/544 |
| 2004/0163648 A1 * | 8/2004 | Burton | 128/204.21 |
| 2005/0199237 A1 | 9/2005 | Lurie | |
| 2006/0009705 A1 | 1/2006 | Brown | |
| 2006/0100538 A1 | 5/2006 | Genger et al. | |
| 2011/0132370 A1 * | 6/2011 | Farrugia | 128/204.23 |

OTHER PUBLICATIONS

Written Opinion of the International Searching Authority for PCT/AU2007/000172, Mar. 2007.

Leiter, Lawrence A. et al., Assessment of the Impact of Fear of Hypoglycemic Episodes on Glycemic and Hypoglycemia Management, Canadian Journal of Diabetes, vol. 29(3), 2005, pp. 186-192.

Meslier, N. et al., Impaired Glucose-Insulin Metabolism in Males with Obstructive Sleep Apnoea Syndrome, European Respiratory Journal, vol. 22(1), 2003, pp. 156-160.

* cited by examiner

METHOD AND APPARATUS FOR MONITORING THE CONDITION OF A PATIENT WITH DIABETES

CROSS-REFERENCE TO RELATED APPLICATION

This application is the U.S. national phase of International Application No. PCT/AU2007/000172 filed 16 Feb. 2007 which designated the U.S. and claims the benefit of Australian Patent Application No. 2006 900780, filed Feb. 17, 2006, the entire contents of each of which are incorporated herein by reference in its entirety.

FIELD OF THE INVENTION

Certain example embodiments described herein relate to the monitoring of diabetic patients and, more particularly, certain example embodiments described herein relate to monitoring diabetic patients during sleep.

BACKGROUND OF THE INVENTION

Sleep-Disordered Breathing (SDB) is a general term for a sleep disorder with apneas and hypopneas. Obstructive Sleep Apnea (OSA) is an example of such a sleep disorder. Sullivan invented treatment of OSA with nasal Continuous Positive Airway Pressure (CPAP). See U.S. Pat. No. 4,944,310 (Sullivan). An apparatus for CPAP treatment typically includes: (i) a source of air at positive pressure, such as a blower, flow generator, or other positive airway pressure (PAP) device; (ii) an air delivery conduit; and (iii) a patient interface, such as a mask. The patient interface typically is connected to the patient with headgear including, for example, a series of elastic straps. At least a portion of the headgear is in contact with the patient's skin, typically on the patient's face. Patients wear the apparatus while sleeping.

A basic CPAP device may provide a supply of air at a generally fixed pressure in the range of 4-20 cmH$_2$O. A more advanced CPAP device such as ResMed's AUTOSET SPIRIT can monitor the patient's breathing, determine the shape of the breath waveform, detect the presence of snoring, apneas, and hypopneas, and also adjust the treatment pressure. See U.S. Pat. No. 5,704,345 (Berthon-Jones), the entire contents of which is incorporated herein by reference.

Diabetes is a disease characterized by an elevated level of glucose in the blood and in the urine. When blood sugar extremes—both high (hyperglycemia) and low (hypoglycemia)—are not treated, a patient can fall into a diabetic coma. The most common cause of diabetic coma is hypoglycemia. This is caused by excessive treatment with insulin relative to food intake and physical activity. Research indicates that the frequency of severe hypoglycemia is about 1.9 and 2.6 episodes per patient per year for Type 1 and Type 2 diabetes patients, respectively, with approximately 50% of these episodes occurring during sleep. There is evidence that the fear of a hypoglycemic episode significantly affects patient outcomes, such as glycemic control and management, self-treatment modifications, and post-episode lifestyle infringements (see Leiter et al. 2005, *Canadian J Diabetes*; 29:186-192). Recent studies have indicated that about 30% of diabetic patients also have OSA (Meslier et al, *Eur. Resp. J*, 22(1): 156-160), and there is emerging data indicating that effective treatment of OSA with n-CPAP significantly improves glucose metabolism.

Given that many diabetic patients will require treatment for their OSA or other SDB, certain example embodiments of the present invention are directed towards improving patient outcomes by providing methods and apparatuses that can reduce the patients' fear of hypoglycemia and/or other diabetes-related events.

SUMMARY OF THE INVENTION

One aspect of certain example embodiments of the invention is to provide an apparatus comprising a hypoglycemia detector and an action unit. In one form, the hypoglycemia detector monitors for one or more of the following: shallow patient breathing, rapid heart rate, temperature, and sweating and, when it detects conditions indicative of hypoglycemia, it sends a signal to the action unit. In one form, the action unit generates a local and/or external alarm upon receipt of a signal from the detector.

According to certain example embodiments, an apparatus for treatment of a patient with both sleep-disordered breathing and diabetes is provided. Such an apparatus may comprise a blower configured to provide a supply of air at positive pressure; a patient interface; headgear to hold the patient interface in position in communication with a patient's airways; at least one hypoglycemia sensor; and an alarm. A controller also may be provided, with the controller being programmed to receive a signal from the at least one hypoglycemia detector, analyze the signal for indications of hypoglycemia, and upon detection of an indication of hypoglycemia trigger the alarm.

According to certain other example embodiments, an apparatus for treatment of a patient with both sleep-disordered breathing and diabetes is provided. A positive airway pressure (PAP) device configured to provide a supply of pressurized breathable gas is provided. At least one glycemia sensor also is provided. A controller is operable to receive a signal from the at least one glycemia detector and is further operable to analyze the signal for an indication of a glycemia abnormality (e.g., hypoglycemia, hyperglycemia, diabetic coma, etc.).

According to still other embodiments, a method of treating a patient with both sleep-disordered breathing and diabetes is provided. A supply of pressurized breathable gas is provided to the patient. A signal indicative of whether the patient is experiencing a diabetic event is generated. Optionally, when the signal indicates that the patient is experiencing a diabetic event, an alert mechanism may be activated and/or a corresponding treatment may be administered.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
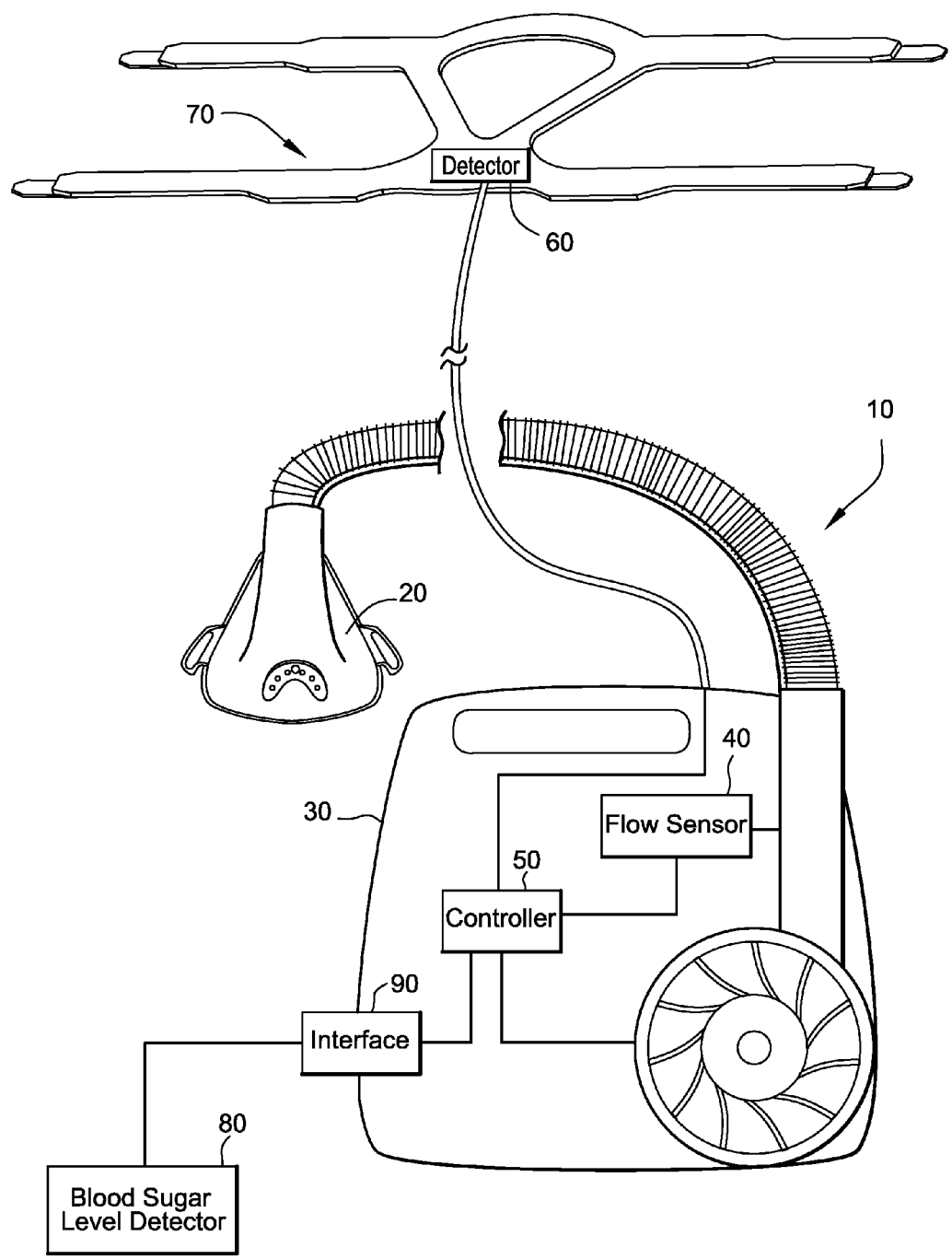
FIG. 1 is an apparatus including a positive airway pressure (PAP) device, patient interface, headgear, and glucose sensor, in accordance with an example embodiment.

In one example embodiment an apparatus 10 includes a patient interface—for example, a nasal mask 20—connected to a positive airway pressure (PAP) device 30 including a flow sensor 40. Patient breathing in the nasal mask 20 is detected by the flow sensor 40, which generates a flow signal that is sent to the controller 50. The controller 50 includes a microprocessor or any suitable combination of hardware, software, or other programmed logic circuitry operable to analyze signals from a range of inputs. In the controller 50, components of the flow signal caused by leak may be filtered (e.g., reduced and/or removed), thereby providing a respiratory flow signal. The heart rate is detected from small oscillations in the flow signal occurring in a frequency band around 1 Hz. Ventilation is determined from the respiratory flow signal.

In certain example embodiments, the apparatus 10 may include a detector 60 built into the headgear 70. In certain example embodiments, the headgear 70 may further comprise skin conductivity sensors in one or more locations in the headgear 70. Such skin conductivity sensors may be arranged so as to be in contact with the skin. Patient sweating can be detected as a change in skin conductivity. In certain example embodiments, the headgear 70 may further include skin temperature sensors. More generally, in certain example embodiments, sensors may be built into and/or otherwise connected to the headgear 70 to detect indications of sympathetic nervous system activation. See, for example, U.S. Publication No. 2006/0100538, the entire contents of which are incorporated herein by reference.

In certain example embodiments, a hypoglycemic detector may be provided, which may include a transcutaneous blood sugar level detector 80 connected to the controller 50 via an interface 90. In certain example embodiments, the blood sugar level detector 80 may include a sensor on a nasal prong for contact with the mucosal regions of the nares. In certain other example embodiments, the sensor may be suitable to be used on a limb of a patient, such as an arm.

In certain example embodiments, the hypoglycemic detector may measure the glucose level in a small amount of interstitial fluid that has been removed from between the skin cells by a vacuum action.

In certain example embodiments, the hypoglycemic detector may use a plethysmogram to detect a range of patient parameters including heart rate. See, for example, PCT Patent Application No. PCT/AU2005/001543 (Martin & Oates), the entire contents of which is hereby incorporated herein by reference.

In certain example embodiments, the hypoglycemic detector may use an electroencephalogram (EEG) to determine when a patient is in a coma. The EEG sensors may be built into the headgear, for example, by using a device manufactured by Advanced Brain Monitoring, Inc.

In certain example embodiments, an action unit is provided, which includes a buzzer that generates an audible signal when hypoglycemia is detected by the detector. In certain other example embodiments, the action unit is connected to a remote monitoring station via a network (e.g., the Internet, a LAN, a WAN, etc.). When hypoglycemia is detected, the action unit may send a signal to the remote monitoring station to indicate that the patient is potentially suffering from a diabetic coma. It will be appreciated that the alarm may include one or more of an audible and/or visual alert, a remote notification, an automated delivery of a treatment (e.g., insulin), etc.

In certain example embodiments, the action unit may further include a drug delivery unit that can supply glucose or insulin, as appropriate, to the person. For example, patients suffering from hypoglycemia may be given glucose, hyperglycemic patients may receive oral insulin via the mask, etc.

Figure 2:
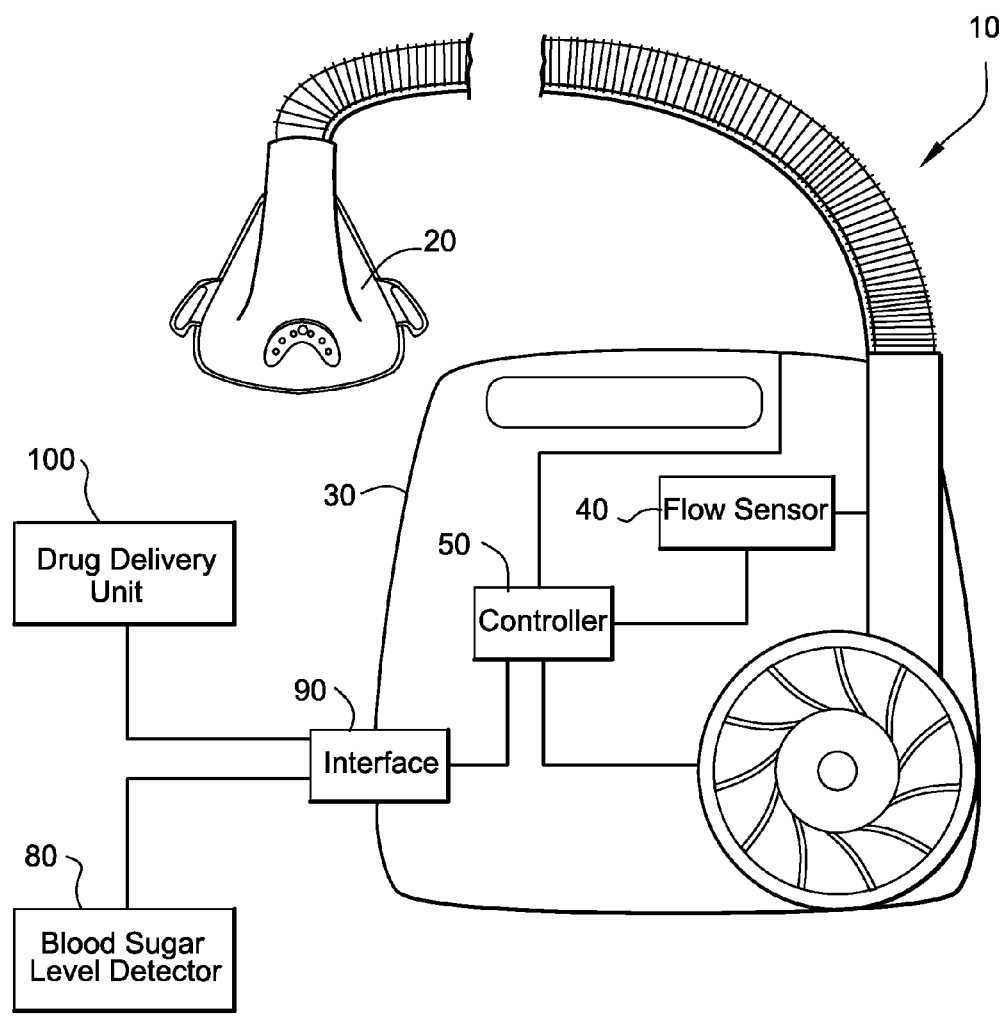
FIG. 2 is an apparatus for treating a patient with both sleep-disordered breathing and diabetes, in accordance with another example embodiment; and, FIG. 3 is an illustrative flowchart showing a procedure for treating a patient with both sleep-disordered breathing and diabetes.

Similar to FIG. 1, FIG. 2 is an apparatus for treating a patient with both sleep-disordered breathing and diabetes, in accordance with another example embodiment. As shown in FIG. 2, a drug delivery unit 100 may be provided to the apparatus which is shown without the headgear 70. Based on the signals at one or more of the flow sensor 40, the blood sugar level detector 80, etc., the controller 50 may determine that a diabetic event (e.g., hypoglycemia, hyperglycemia, diabetic coma, etc.), apnea or hypopnea event, and/or other events has/have occurred. In response, the controller 50 may, via the interface 40, instruct the drug delivery unit 100 to supply a treatment to the patient. For example, oral insulin, glucose, etc. may be administered automatically (e.g., via a vapor and/or aerosol delivery) and/or recommended for administration by a human user.

Figure 3:
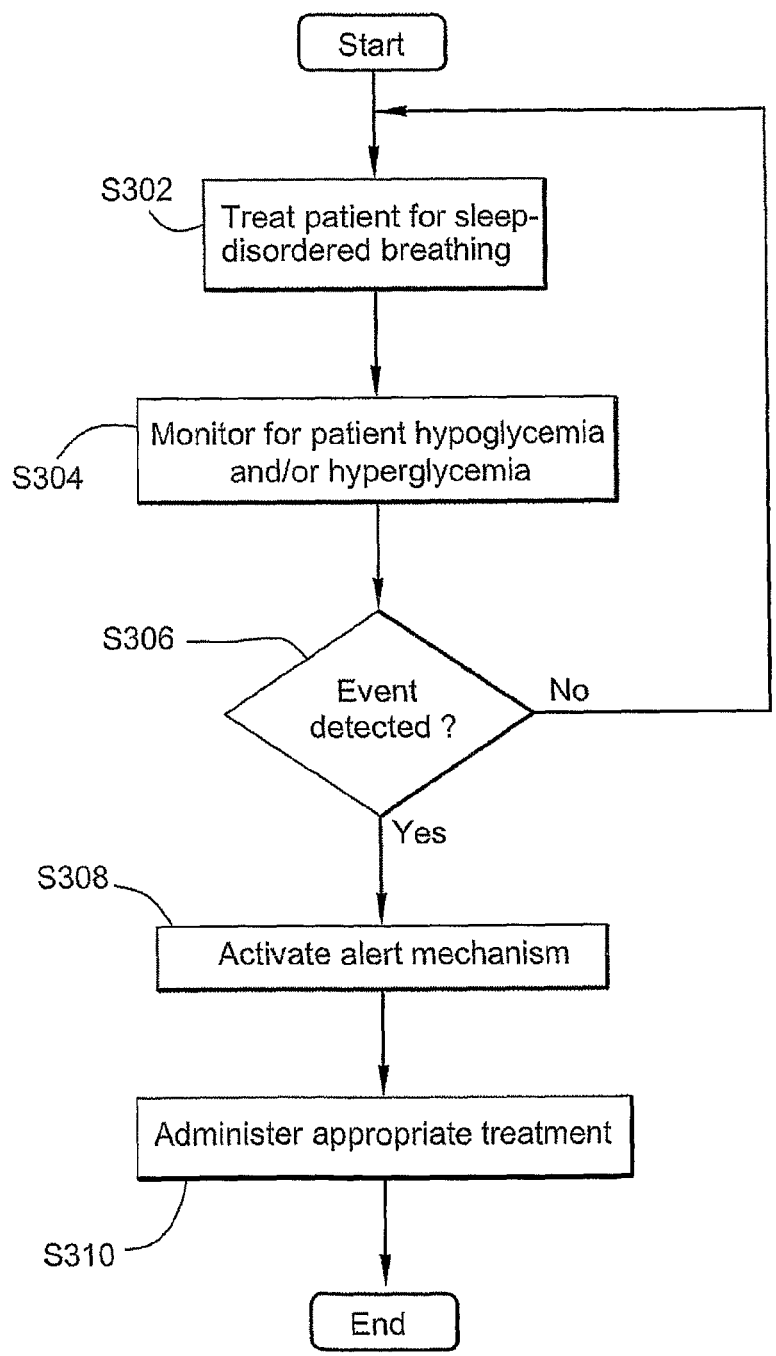

FIG. 3 is an illustrative flowchart showing a procedure for treating a patient with both sleep-disordered breathing and diabetes. In FIG. 3, a patient is treated for sleep-disordered breathing in step S302. Monitoring for hypoglycemia and/or hyperglycemia is performed in step S304. The monitoring process may include gathering relevant signals (e.g., patient sweat, heart rate, EEG signals, breath, snore, blood sugar level, etc.) and/or filtering such signals when necessary. If a diabetic event is not detected in step S306, the normal treatment and monitoring continues. However, if a diabetic event is detected in step S306, an alert mechanism is activated in step S308. As noted above, the alert mechanism may include, for example, activating an audio/visual alarm, notifying a monitoring station that may be located remote from the patient, etc. Additionally, an appropriate treatment may be administered in step S310.

Given these techniques, patients suffering from both OSA and/or other sleep-disordered breathing and diabetes who are being treated with nasal CPAP can sleep with the assurance that should they begin to become hypoglycemic, their CPAP device will detect this and raise an alarm and/or take a suitable counteraction.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An apparatus for treatment of a patient with both sleep-disordered breathing and diabetes, comprising:
   a blower configured to provide a supply of air at positive pressure;
   a patient interface including a mask;
   headgear adapted to hold the patient interface in position in communication with a patient's airways;

at least one hypoglycemia detector including a sensor for contact with mucosal regions of the patient's nares on a nasal prong of the mask;
an alarm; and
a controller,
wherein the controller is programmed to receive a signal from the at least one hypoglycemia detector, analyze the signal for indications of hypoglycemia and, upon detection of an indication of hypoglycemia, trigger the alarm.

2. The apparatus according to claim 1, wherein said at least one hypoglycemia detector is further configured to detect activation of the sympathetic nervous system.

3. The apparatus according to claim 1, wherein said at least one hypoglycemia detector is further configured to detect at least one of: patient sweating, temperature, heart rate, and respiration rate.

4. The apparatus according to claim 1, further comprising a flow sensor in fluid communication with the patient interface.

5. The apparatus according to claim 1, wherein said alarm is a buzzer.

6. The apparatus according to claim 1 wherein said alarm is sent to a remote monitoring system.

7. An apparatus for treatment of a patient with both sleep-disordered breathing and diabetes, comprising:
a PAP device configured to provide a supply of pressurized breathable gas;
at least one glycemia detector built into a mask system connected to the PAP device; and,
a controller operable to receive a signal from the at least one glycemia detector and further operable to analyze the signal for an indication of a glycemia abnormality,
wherein the at least one glycemia detector further includes:
a transcutaneous blood sugar level detector, a sensor for contact with mucosal regions of the patient nares on a nasal prong of a mask connected to the PAP device, and/or a sensor configured to measure the patient's glucose level by extracting a small amount of interstitial fluid that has been removed from between the skin cells via a vacuum tube.

8. The apparatus according to claim 7, wherein said at least one glycemia detector is further configured to detect activation of the sympathetic nervous system.

9. The apparatus according to claim 7, wherein said at least one glycemia detector is further configured to detect at least one of: patient sweating, temperature, heart rate, and respiration rate.

10. The apparatus according to claim 7, wherein the controller is further operable to sound an audible alert when the signal indicates a glycemia abnormality.

11. The apparatus according to claim 7, wherein the controller is further operable to send information about the patient treatment to a remote monitoring station.

12. The apparatus according to claim 11, wherein the controller is configured to send the information when the signal indicates one or more of: patient hypoglycemia, hyperglycemia, and/or diabetic coma.

13. The apparatus according to claim 7, further comprising a drug delivery unit.

14. The apparatus according to claim 13, wherein the drug delivery unit is configured to supply glucose and/or insulin to the patient.

15. A method of treating a patient with both sleep-disordered breathing and diabetes, the method comprising:
providing a supply of pressurized breathable gas to the patient; and,
generating a signal indicative of whether the patient is experiencing a diabetic event, the signal being based on data gathered from (a) a first sensor in contact with mucosal regions of the patient's nares on a nasal prong of a mask connected to a PAP device used in providing the supply of pressurized breathable gas to the patient, and (b) a second sensor built into headgear that is adapted to hold the mask in a position suitable for communicating the supply of pressurized breathable gas to the patient's airways.

16. The method according to claim 15, further comprising when the signal indicates that the patient is experiencing a diabetic event, activating an alert mechanism.

17. The method according to claim 16, wherein the activating of the alert mechanism is further practiced by sounding an audible alarm.

18. The method according to claim 16, wherein the activating of the alert mechanism is further practiced by notifying a remote monitoring station.

19. The method according to claim 15, further comprising when the signal indicates that the patient is experiencing a diabetic event, administering a corresponding treatment.

20. The apparatus according to claim 7, wherein the at least one glycemia detector is built into headgear that is adapted to hold the mask in a position suitable for communicating the supply of pressurized breathable gas to the patient's airways.

21. The apparatus according to claim 7, wherein the at least one glycemia detector includes a sensor for contact with mucosal regions of the patient nares on a nasal prong of a mask connected to the PAP device.

22. An apparatus for treatment of a patient with both sleep-disordered breathing and diabetes, comprising:
a PAP device including a controller, the PAP device being configured to provide a supply of air at positive pressure at 4-20 cmH$_2$O;
a patient interface;
headgear adapted to hold the patient interface in position in communication with a patient's airways;
at least one hypoglycemia detector, wherein the at least one hypoglycemia detector includes a sensor for contact with mucosal regions of the patient nares on a nasal prong of the patient interface connected to the PAP device; and
an alarm;
wherein the controller included in the PAP device is programmed to receive a signal from the at least one hypoglycemia detector, analyze the signal for indications of hypoglycemia and, upon detection of an indication of hypoglycemia, trigger the alarm.

23. An apparatus for treatment of a patient with both sleep-disordered breathing and diabetes, comprising:
a PAP device configured to provide a supply of pressurized breathable gas at one or more sleep-disordered breathing treatment pressures in a range of 4-20 cmH$_2$O;
at least one glycemia detector, wherein the at least one glycemia detector includes a sensor for contact with mucosal regions of the patient nares on a nasal prong of a patient interface connected to the PAP device;
an action unit including a drug delivery unit for use in treating the patient's diabetes; and
a controller integrated into the PAP device and operable to receive a signal from the at least one glycemia detector, analyze the signal for an indication of a glycemia abnormality, and instruct the drug delivery unit to provide a treatment to the patient for the glycemia abnormality while also instructing the PAP device to provide the supply of pressurized breathable gas.

24. The apparatus according to claim 23, wherein the drug delivery unit is configured to provide oral insulin and/or glucose to the patient upon receiving instructions from the controller.

25. The apparatus according to claim 23, wherein the drug delivery unit is configured to provide the treatment to the patient for the glycemia abnormality in vapor form and/or through aerosol delivery.

26. The apparatus according to claim 23, wherein the drug delivery unit is configured to provide insulin and/or glucose to the patient in vapor form and/or through aerosol delivery upon receiving instructions from the controller.

* * * * *

UNITED STATES PATENT AND TRADEMARK OFFICE
CERTIFICATE OF CORRECTION

PATENT NO.        : 8,640,698 B2                                    Page 1 of 1
APPLICATION NO. : 11/997976
DATED             : February 4, 2014
INVENTOR(S)       : Darkin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1555 days.

Signed and Sealed this
Twenty-second Day of September, 2015

Michelle K. Lee
*Director of the United States Patent and Trademark Office*